(12) United States Patent
Mathews et al.

(10) Patent No.: US 11,400,261 B2
(45) Date of Patent: Aug. 2, 2022

(54) PREFORMED GUIDEWIRE

(71) Applicant: Concert Medical, LLC, Norwell, MA (US)

(72) Inventors: Eric D. Mathews, Walpole, MA (US); John R. Panicci, Plymouth, MA (US); Mark W. I. Webster, Auckland (NZ)

(73) Assignee: CONCERT MEDICAL, LLC, Norwell, MA (US)

( * ) Notice: Subject to any disclaimer, the term of this patent is extended or adjusted under 35 U.S.C. 154(b) by 0 days.

(21) Appl. No.: 14/646,431

(22) PCT Filed: Nov. 21, 2013

(86) PCT No.: PCT/US2013/071259
§ 371 (c)(1),
(2) Date: May 21, 2015

(87) PCT Pub. No.: WO2014/081942
PCT Pub. Date: May 30, 2014

(65) Prior Publication Data
US 2015/0290432 A1   Oct. 15, 2015

Related U.S. Application Data

(60) Provisional application No. 61/796,861, filed on Nov. 21, 2012.

(51) Int. Cl.
*A61M 25/09* (2006.01)
*A61F 2/24* (2006.01)
*A61M 25/00* (2006.01)

(52) U.S. Cl.
CPC ........... *A61M 25/09* (2013.01); *A61F 2/2436* (2013.01); *A61M 25/0041* (2013.01);
(Continued)

(58) Field of Classification Search
CPC ........ A61M 25/09; A61M 2025/09175; A61M 2025/09083; A61M 2025/09133;
(Continued)

(56) References Cited

U.S. PATENT DOCUMENTS 4,607,746 A * 8/1986 Stinnette ............. A61M 25/002
                                                              206/363
4,917,102 A    4/1990 Miller et al.
(Continued)

FOREIGN PATENT DOCUMENTS

EP    0260711 A2    3/1988
EP    0769306 A2    4/1997
(Continued)

OTHER PUBLICATIONS

Website entitled "Heart Suncatcher" by WigJig.com Sep. 26, 2012. Retrieved from <http://web.archive.org/web/20120926111335/http://wigjig.com/holiday-designs/valentines-day/259-heart-suncatcher> on Jan. 16, 2017.*
(Continued)

*Primary Examiner* — David J. McCrosky
(74) *Attorney, Agent, or Firm* — Kriegesman & Kriegsman

(57) ABSTRACT

A preformed guidewire particularly well-suited for use in percutaneous medical procedures, such as transcatheter aortic valve replacement, includes an inner corewire of discontinuous, tapered stiffness that is surrounded along a portion of its length by a flexible, outer casing of uniform cross-section, such as a tightly wound, stainless steel, spring coil wire. The inner corewire is constructed of a shape-memory material, such as a nickel-titanium alloy, that is preformed into an encircled S-shaped configuration in its atraumatic distal region. Specifically, the distal region includes an enlarged, stiffened, proximate segment that encircles a
(Continued)

smaller, more flexible, distal segment. As a feature of the invention, the distal and proximal segments project along fixed-radial arcuate paths that extend in opposite directions from one another. As a result, the distal region is optimally configured to limit the risk of trauma to the immediate site of treatment when inserted through a straightened guide catheter.

14 Claims, 6 Drawing Sheets

(52) U.S. Cl.
CPC ............ *A61M 2025/09066* (2013.01); *A61M 2025/09083* (2013.01); *A61M 2025/09133* (2013.01); *A61M 2025/09175* (2013.01)

(58) Field of Classification Search
CPC ........... A61M 2025/09183; A61M 2025/0915; A61M 2025/09075; A61F 2/2436
USPC ...................................................... 600/585
See application file for complete search history.

(56) References Cited

U.S. PATENT DOCUMENTS

| | | | |
|---|---|---|---|
| 4,925,445 A | 5/1990 | Sakamoto et al. | |
| 5,129,890 A | 7/1992 | Bates et al. | |
| 5,295,493 A | 3/1994 | Radisch, Jr. | |
| 5,322,509 A * | 6/1994 | Rickerd | A61M 25/0041 600/435 |
| 5,551,443 A | 9/1996 | Sepetka et al. | |
| 5,584,843 A | 12/1996 | Wulfman et al. | |
| 5,647,127 A * | 7/1997 | Miyata | A61M 25/09 228/156 |
| 5,807,339 A * | 9/1998 | Bostrom | A61M 25/0041 604/164.01 |
| 5,846,210 A * | 12/1998 | Ogawa | A61B 17/12022 600/585 |
| 6,074,378 A | 6/2000 | Mouri et al. | |
| 6,254,550 B1 | 7/2001 | McNamara et al. | |
| 6,391,018 B1 | 5/2002 | Tanaka et al. | |
| 6,491,648 B1 | 12/2002 | Cornish et al. | |
| 6,500,185 B1 | 12/2002 | Mathews et al. | |
| 6,620,172 B1 | 9/2003 | Dretler et al. | |
| 6,652,536 B2 | 11/2003 | Mathews et al. | |
| 7,058,456 B2 | 6/2006 | Pierce | |
| 7,169,118 B2 * | 1/2007 | Reynolds | A61M 25/09 600/585 |
| 7,618,379 B2 * | 11/2009 | Reynolds | A61L 31/022 600/433 |
| 7,789,839 B2 * | 9/2010 | Lupton | A61M 25/09 600/585 |
| 8,500,697 B2 * | 8/2013 | Kurth | A61M 25/09 600/585 |
| 9,968,761 B2 | 5/2018 | Brecker | |
| 2003/0139689 A1 | 7/2003 | Shturman et al. | |
| 2004/0073141 A1 | 4/2004 | Hartley et al. | |
| 2004/0129352 A1 | 7/2004 | Shiota | |
| 2005/0065456 A1 | 3/2005 | Eskuri | |
| 2006/0116609 A1 | 6/2006 | Kanuka et al. | |
| 2007/0032831 A1 | 2/2007 | Eigler et al. | |
| 2007/0225784 A1 | 9/2007 | Bly et al. | |
| 2008/0097465 A1 | 4/2008 | Rollins et al. | |
| 2009/0105724 A1 * | 4/2009 | Yoshizaki | A61M 25/0041 606/129 |
| 2009/0209987 A1 | 8/2009 | Mathews et al. | |
| 2010/0094310 A1 | 4/2010 | Warring et al. | |
| 2012/0016342 A1 | 1/2012 | Brecker | |
| 2012/0041420 A1 * | 2/2012 | Nagano | A61M 25/09 604/528 |
| 2012/0041422 A1 | 2/2012 | Whiting et al. | |
| 2012/0191064 A1 | 7/2012 | Conston, Sr. et al. | |

FOREIGN PATENT DOCUMENTS

| | | | |
|---|---|---|---|
| EP | 0778043 A1 | 6/1997 | |
| EP | 0515201 B1 | 9/1997 | |
| EP | 1105181 B1 | 2/2004 | |
| EP | 1920795 A1 | 5/2008 | |
| EP | 1419797 B1 | 6/2008 | |
| EP | 1992383 A1 | 11/2008 | |
| EP | 2135638 A1 | 12/2009 | |
| JP | H07255856 A1 | 10/1995 | |
| WO | 9903426 A1 | 1/1999 | |
| WO | 0032265 A1 | 6/2000 | |
| WO | 0117601 A1 | 3/2001 | |
| WO | 0205886 A1 | 1/2002 | |
| WO | 2004018031 A2 | 3/2004 | |
| WO | WO 2004110519 A2 * | 12/2004 | ............ A61M 25/09 |
| WO | 2007006055 A2 | 1/2007 | |
| WO | WO 2010092347 A1 * | 8/2010 | ............ A61M 25/09 |

OTHER PUBLICATIONS

Roy et al., "First-in-man assessment of a dedicated guidewire for transcatheter aortic valve implantation," EuroIntervention, 8:1019-1025 (2013).
Chieffo et al., "A 'Modified Wire' To Prevent Cardiac Perforation During TAVI 'First-In-Man,'" Angioplasty Summit TCTAP 2012, Seoul, Korea (Apr. 24-27, 2012).
European Search Report dated Jun. 29, 2016, in corresponding European Patent Application No. 13856589.0.

* cited by examiner

PREFORMED GUIDEWIRE

FIELD OF THE INVENTION

The present invention relates generally to the field of percutaneous medical procedures and more particularly to guidewires utilized in percutaneous medical procedures.

BACKGROUND OF THE INVENTION

Guidewires are well known in the art and are commonly utilized in a wide variety of percutaneous medical procedures including, but not limited to, gastrointestinal, hepatobiliary and cardiac procedures.

One area where percutaneous guidewires are finding a distinct use is in the field of transcatheter aortic valve implantation (TAVI). As part of the medical procedure, the guidewire is inserted through a guide catheter that is positioned within the aortic valve of the patient. The guidewire is then advanced through the guide catheter until the atraumatic distal end of the guidewire locates, or nests, against the base of the left ventricle. With the guidewire positioned inside the heart in the manner set forth above, the guide catheter is then removed from the patient. Accordingly, the guidewire thus serves as a support structure for the medical procedure. In this capacity, the guidewire can be used to reliably guide catheters, endoscopes, implants and other similar delivery systems to the site.

The particular environments in which percutaneous guidewires are utilized tend to place conflicting constraints on their design. In particular, guidewires utilized in coronary procedures, such as transcatheter aortic valve implantation, are typically designed with a sufficient degree of flexibility in order to facilitate negotiation of tortuous anatomy and to minimize trauma to the heart. At the same time, guidewires used in coronary procedures, such as transcatheter aortic valve implantation, need to maintain a certain level of stiffness, particularly in the region of treatment, in order to provide adequate support for items delivered thereon (e.g., aortic valve implantation systems) and to sit comfortably within the left ventricle in a stable, atraumatic manner.

Most modern guidewires utilized in coronary procedures, such as TAVI procedures, include a relatively rigid inner corewire, or core, that is surrounded by a relatively flexible outer casing with a generally uniform outer diameter along the majority of its length. The outer casing is permanently secured to the corewire at each of its ends using an appropriate bonding agent, such as solder or epoxy, to render the guidewire unitary in its construction.

The corewire for a TAVI guidewire is commonly manufactured using a straight wire that is constructed of a relatively stiff material, such as stainless steel. The distal tip of the corewire typically extends slightly beyond the corresponding end of the outer casing and is commonly provided with a soft, bulbous construction to limit the risk of direct trauma to the patient.

However, it has been found that, even with its softened, bulbous construction, the distal tip of the corewire can still cause significant trauma to the patient. Accordingly, the corewire is commonly provided with a couple additional design features to render the guidewire less likely to puncture, or otherwise damage, sensitive myocardial tissues and structures.

As a first design feature, the stiffness of the guidewire is often decreased subtly towards the distal end by gradually reducing the cross-sectional diameter of the corewire. In this manner, the distal end of the guidewire is provided with sufficient flexibility, deformability and general softness to minimize the risk of ventricular perforation and pericardial effusion. At the same time, the region of the guidewire that locates within the aortic valve is provided with a greater degree of stiffness, thereby providing adequate support at the site of the procedure. It should be noted that the subtle transition in flexibility is provided to render the guidewire more resistant to kinking upon the application of stress thereto. As can be appreciated, it has been found that regions in the corewire with rapid transitions in wire flexibility are more susceptible to the formation of a sharpened bends, or kinks, during use. The creation of sharpened bends in the guidewire is problematic in that such bends can (u) introduce traumatic forces against a point on the ventricle wall, thereby perforating or otherwise damaging the myocardium, and (ii) catch on a device slidably mounted thereon, such as a guide catheter or valve implant.

As a second feature, the distal region of the corewire is commonly shaped by the physician prior to surgery to include a long, gentle bend that further limits the risk of damage to delicate tissue during introduction and positioning of the guidewire within the patient. As can be appreciated, the introduction of an elongated resilient bend minimizes the likelihood of trauma to the patient by transmitting forces applied to myocardial tissues and structures by the guidewire along a dispersed, inwardly deflecting, or radial, path rather than along a concentrated, longitudinal path on the corewire tip.

The aforementioned practice of utilizing a guidewire which includes a generally straight, stainless steel corewire that is manually bent by the physician prior to use has been found to experience a notable drawback. Specifically, physician bent guidewires have been found to lose some of its imparted shape during advancement through the guide catheter to the treatment site. As a result, the distal region of the guidewire often assumes a potentially harmful configuration within the left ventricle, which is highly undesirable.

Accordingly, as part of a recent trend, preformed guidewires are prominently used in percutaneous medical procedures. Preformed guidewires differ from traditional guidewires in that the corewire is constructed of a super elastic, shape-memory material, such as a metal alloy of nickel and titanium that is commonly referred to in the art as nitinol. The preformed guidewire is then appropriately shaped as part of the manufacturing process, rather than by the physician. It is to be understood that the use of a shape-memory material enables the distal region of the guidewire to maintain its optimized configuration even after being passed through the guide catheter.

In U.S. Pat. No. 6,254,550 to T. O. McNamara et al., the disclosure of which is incorporated herein by reference, there is shown a preformed guidewire that includes a tapered distal portion over which a spring coil wire is attached to provide radiopacity and safety to the vasculature. The distal portion of the wire guide is flexible and is further made atraumatic by the addition of a hook-shaped or "J" tip. By directing the distal tip inward, the bend, or curvature, created in the guidewire is thereby exposed for contact rather than the distal tip. Although the tip is rounded and buffed to minimize potential trauma, it has been found that the curvature created in the guidewire is more aptly suited to absorb contact against sensitive tissue by imparting a less concentrated, deflecting radial force.

In U.S. Patent Application Publication No. 2012/0016342 to S. Brecker, the disclosure of which is also incorporated herein by reference, there is shown a percutaneous guidewire comprising a distal end portion that is pre-formed in a curve that turns through more than 270 degrees and that, in one embodiment, turns at least 540 degrees in a spiraled configuration.

Although well-known and widely used in the industry, preformed guidewires of the type as described above that curve in one direction to create a generally J-shaped or spiral-shaped configuration at its distal end have been found to suffer from a notable shortcoming. Specifically, the one-directional curvature of the distal end of the guidewire can inadvertently result in pericardium perforation. Specifically, as the guidewire is advanced through the guide catheter and into the left ventricle, the tip of the guidewire may be directed in such a manner so as to catch on the pericardium. Due to its one-directional curvature, the continued advancement of the guidewire causes the tip to further engage and effectively pull the pericardium on which it is caught, thereby resulting in significant trauma to the patient.

SUMMARY OF THE INVENTION

It is an object of the present invention to provide a new and improved guidewire for use in percutaneous medical procedures.

It is another object of the present invention to provide a guidewire of the type as described above that is particularly well-suited for use in coronary procedures, such as transcatheter aortic valve implantation.

It is yet another object of the present invention to provide a guidewire of the type as described above that has a preformed distal end that is configured to minimize the risk of patient trauma.

It is still another object of the present invention to provide a guidewire of the type as described above that has a limited number of parts, is inexpensive to manufacture and is easy to use.

Accordingly, there is provided a preformed guidewire comprising an inner corewire, the inner corewire including a proximal region and a distal region, the distal region terminating into an atraumatic tip, wherein the distal region includes a proximal segment and a distal segment, the proximal and distal segments extending along paths that curve in opposite directions.

Various other features and advantages will appear from the description to follow. In the description, reference is made to the accompanying drawings which form a part thereof, and in which is shown by way of illustration, various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts:

FIGS. 5(a)-(d) are fragmentary front views of the preformed guidewire shown in FIG. 1 at various stages during its advancement through a guide catheter, the preformed guidewire being shown inserted into the left ventricle of a heart to illustrate the benefits of its design, details in the outer cover not being shown for ease of illustration.

DETAILED DESCRIPTION OF THE INVENTION

Figure 1:
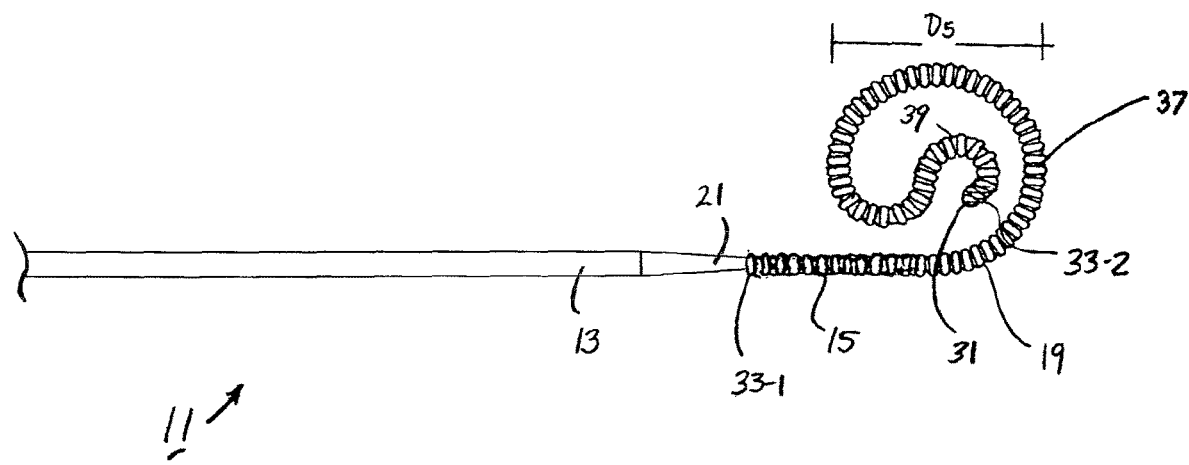
FIG. 1 is a fragmentary, top view of a preformed guidewire constructed according to the teachings of the present invention.
Figure 2:
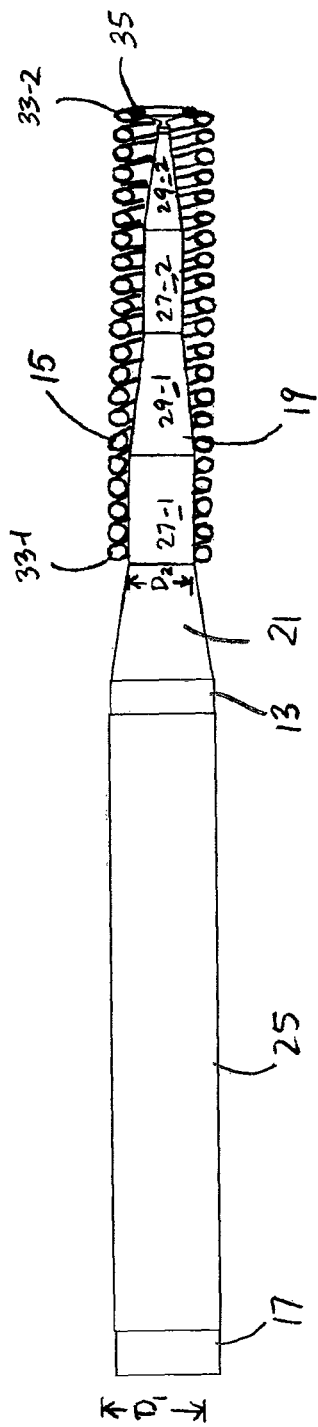
FIG. 2 is a top view of the preformed guidewire shown in FIG. 1, the guidewire being shown in straightened form and out of proper dimensional scaling for ease of illustration, the outer casing being shown in longitudinal cross-section to display the details of the corewire.

Referring now to FIGS. 1 and 2, there is shown a preformed guidewire that is constructed according to the teachings of the present invention, the guidewire being identified generally by reference numeral 11. As will be explained further below, preformed guidewire 11 is specifically designed to serve as a support structure for the percutaneous delivery of medication, medical instruments, implantation devices and/or other related systems to a site of treatment while, at the same time, limiting the risk of direct trauma to the patient.

In the description that follows, preformed guidewire 11 is shown as having a design that is optimized for use in connection with a transcatheter aortic valve implantation (TAVI) procedure. However, it should be noted that guidewire 11 is not limited to use in TAVI procedures. Rather, it is to be understood that guidewire 11 could be similarly utilized in a wide variety of percutaneous medical procedures, such as gastrointestinal procedures, hepatobiliary procedures as well as alternative types of coronary procedures, without departing from the spirit of the present invention.

Preformed guidewire 11 comprises an inner corewire 13 that is surrounded along a portion of its length by an outer casing 15.

Inner corewire, or core, 13 is represented herein an elongated, unitary, preformed member with a solid, generally circular shape in transverse cross-section. As will be described further below, corewire 13 is constructed with a fixed diameter $D_1$ of approximately 0.035 inches along the entirety of its length that is grinded down, or otherwise reduced, in selected areas as part of a subsequent manufacturing process in order to modify its flexibility.

As can be seen, corewire 13 includes an elongated, relatively stiff proximal region 17 which is connected to a relatively flexible distal region 19 through a shortened, tapered transition region 21. As will be described further in detail below, distal region 19 is preformed into a uniquely designed, atraumatic configuration that serves as a principal novel feature of the present invention.

As referenced briefly above, corewire 13 is manufactured as a preformed member. Accordingly, corewire 13 is preferably constructed of a superelastic material, such as a nickel-titanium (Ni—Ti) alloy commonly referred to in the an as nitinol. As can be appreciated, the use of a superelastic material enables distal region 19 of corewire 13 to resiliently return to its optimized shape after being passed through a straightened guide catheter at the treatment site.

Proximal region 17 of corewire 13 is preferably not subjected to a subsequent grinding process and, as such, maintains diameter $D_1$ along the entirety of its length. As a consequence, proximal region 17 is of a sufficient rigidity to support the delivery of items to the treatment site. A microthin, polymer, outer coating 25 is preferably applied to the exterior of corewire 13 within proximal region 17 in order to ease advancement of guidewire 11 through a guide catheter as well as facilitate the delivery and withdrawal of devices slid thereover.

Outer coating 25 preferably represents any polymer that is either hydrophilic or has been surface treated with a hydrophilic material to increase lubricity, with the particular material selected based on the needs of the intended application. As an example, outer coating 25 may be in the form of polytetrafluoroethylene (PTPE).

As seen most clearly in FIG. 2, corewire 13 has a gradual, discontinuing reduction in its cross-sectional diameter from transition region 21 through the majority of distal region 19. In this capacity, the subtle narrowing of corewire 13 provides overlapping outer casing 15 with a diminishing degree of stiffness towards its distal end. Accordingly, by enhancing its flexibility, distal region 19, which is designated for placement against sensitive myocardial tissues and structures, is less able to impart potentially harmful forces. At the same time, both proximal region 17 and transition region 21 maintain a significant degree of stiffness, which is critical since these regions are designated for alignment within the aortic valve when inserted into the patient and, as such, require considerable support for the delivery of critical components, such as the replacement aortic valve.

Figure 3:
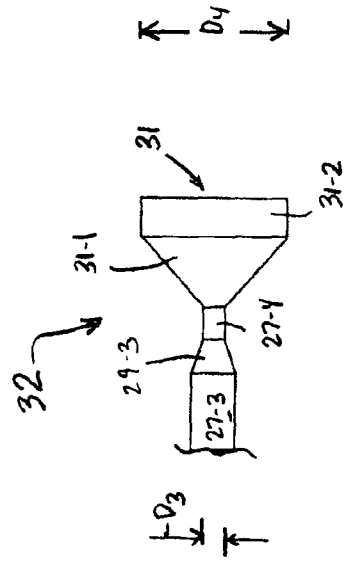
FIG. 3 is an enlarged, fragmentary top view of the tip of the corewire shown in FIG. 2.

Transition region 21, which has a length of approximately 2.3 inches, tapers inward approximately 0.01 inches, thereby resulting in a narrowed outer diameter $D_2$ of approximately 0.025 inches at its distal end. Similarly, as seen in FIGS. 2 and 3, distal region 19 tapers inward in a subtle, discontinuous fashion through an end-to-end series of alternating, variable length, barrel portions 27-1 thru 27-4 and tapered portions 29-1 thru 29-3, with barrel portion 27-4 being provided with a significantly reduced diameter $D_3$ of approximately 0.0045 inches.

Distal region 19 of corewire 13 terminates into a distal enlargement 31 with an outer diameter $D_4$ of approximately 0.015 inches. Enlargement 31 is shaped to include a tapered portion 31-1 formed onto the distal end of short, narrow barrel portion 27-4 and a barrel portion 31-2 formed onto the distal end of tapered portion 31-1.

Together, barrel portions 27-3, 27-4 and 31-2 and tapered portions 29-3 and 31-1 define an atraumatic tip 32 with a modified hourglass, or bowtie-like, design. Due to its considerably short and narrow construction, barrel portion 27-4 acts as a thin neck, or stem, about which enlargement 31 is adapted to freely pivot. Accordingly, upon receiving contact forces, tip 32 is designed to buckle, or pivot, about barrel portion 27-4. As a result, the aforementioned ability of distal region 19 to buckle upon contact thereby limits the degree of trauma tip 32 can impart on sensitive myocardial tissues and structures.

As referenced briefly above, the modification in cross-sectional diameter of corewire 13 is preferably achieved through a grinding process. However, it is to be understood that the reduction in cross-sectional diameter of corewire 13 could be accomplished using other known techniques without departing from the spirit of the present invention.

Referring back to FIGS. 1 and 2, outer casing 15 is constructed as a generally cylindrical member hollowed along its length that includes an open first end 33-1 and an open second end 33-2. Outer casing 15 is permanently secured to corewire 13 at first end 33-1 and second end 33-2 by applying an appropriate bonding agent 35, such as solder or an adhesive, therebetween.

Outer casing 15 is represented herein as a segment of spring coil wire with closely adjacent turns that inherently provides a requisite amount of flexibility. Such a spring coil wire is preferably constructed out of an appropriate formable material, such as stainless steel, that is applied with a lubricious coating on its exterior surface to facilitate advancement and retraction of guidewire 11 through the guide catheter.

As seen in FIG. 2, outer casing 15 preferably maintains a fixed outer diameter $D_1$ of approximately 0.035 inches along the entirety of its length (i.e., the outer diameter of outer casing 15 is equal to the outer diameter of proximal region 17 of corewire 13). In this capacity, outer casing 15 provides tapered distal region 19 of guidewire 11 with a uniform outer diameter that is dimensionally appropriate to support the delivery of transcatheter aortic valve implantation systems.

It should be noted that the particular stiffness of outer casing 15 could be modified to optimize guidewire 11 for use in various types of procedures. For instance, when guidewire 11 is utilized in transcatheter procedures that require a lesser degree of structural support, the stiffness of outer casing 15 could be reduced by reducing the diameter in transverse cross-section, by selecting a more flexible material, and/or by raising the austenitic finish temperature applied thereto during a thermal shaping process to further protect the patient).

It should also be noted that outer casing 15 need not be limited to a spring coil wire formed out of stainless steel. Rather, it is to be understood that outer casing 15 could have an alternative construction without departing from the spirit of the present invention. For instance, outer casing 15 could be in the form of a lubricious polymer jacket with a uniform outer diameter along its length. Additionally, it is to be understood that outer casing 15 (as well as corewire 13) could be provided with a relatively flattened profile in transverse cross-section without departing from the spirit of the present invention.

It should further be noted that the use of a stainless steel material to form outer casing 15 preferably renders the distal end of guidewire 11 radiolucent. Accordingly, outer casing 15 may be applied with a radiopaque surface treatment (e.g., a platinum, palladium, gold, tantalum, or tungsten-based treatment) to render the distal end of guidewire 11 highly visible under fluoroscopy.

As referenced briefly above, distal region 19 of inner corewire 13 is preferably preformed into an optimized atraumatic configuration, with flexible outer casing 15 assuming the shape of corewire 13. As will be described further below, distal region 19 is preformed into a single plane structure that is shaped to include a pair of oppositely curved portions in order to limit trauma to the surgical site, the inclusion and arrangement of the oppositely curved portions serving as a principal novel feature of the present invention.

Specifically, as seen in FIG. 1, distal region 19 of inner corewire 13 is preferably preformed into a single plane, encircled S-shaped configuration that includes an enlarged, relatively stiff proximal segment 37 that extends out from transition region 21 along a primary curved path and a smaller, flexible distal segment 39 that extends out from proximal segment 37 along a secondary curved path that is opposite in direction relative to the primary curved path.

Proximal segment 37 is formed as an enlarged curvature with a generally fixed, or slightly reducing, radius that extends, or bends, in a first direction (counterclockwise as shown in FIG. 1) at least 270 degrees and, in the preferred embodiment, approximately 360 degrees. Preferably, proximal segment 37 has an overall diameter $D_5$ of approximately 1.2 inches. As such, the distal end of guidewire 11 is appropriately dimensioned to facilitate placement in a variety of anatomical spaces, including hypertrophied hearts with smaller ventricular cavities as well as in a descending thoracic aorta.

Distal segment 39 is formed as limited curvature with a generally fixed, or slightly reducing, radius that extends, or bends, from proximal segment 37 in the opposite direction (clockwise as shown in FIG. 1) at least 90 degrees and, in the preferred embodiment, approximately 180 degrees. With distal region 19 preformed in the manner described above, proximal segment 37 extends around, or circumscribes, distal segment 39.

As will be described further in detail below, the reversal in the direction of bending from proximal segment 37 to distal segment 39 introduces a couple notable advantages.

As a first advantage, the bend reversal incorporated into distal region 19 causes tip 32 to locate within the enlarged curvature of proximal segment 37. Positioned in this manner, tip 32 is effectively shielded by proximal segment 37 and, as a result, is and less likely to contact the ventricular wall of the patient and thereby cause trauma to the site.

As a second advantage, the bend reversal incorporated into distal region 19 causes tip 32 (and its surrounding outer casing 15) to initially project through a guide catheter along a primary arcuate path. Further advancement of distal region 19 through the guide catheter causes tip 32 to then reverse direction and travel along a secondary arcuate path that runs in the opposite direction from the primary arcuate path. In this capacity, if tip 32 initially catches on the myocardium, the subsequent reversal in direction causes tip 32 to withdraw from the myocardium, thereby limiting the damage caused thereto. By comparison, prior art guidewires that curve in a single direction would continue to engage and damage the myocardium as the guidewire is further advanced through a guide catheter, as will be explained further below.

It should be noted that distal region 19 need not be constructed as a single plane structure. Rather, it is to be understood that distal region 19 could be alternatively constructed as a multi-planar structure without departing from the spirit of the present invention. In particular, because the space within the left ventricle is multi-planar, distal region 19 could be similarly provided with a multi-planar design.

Figure 4:
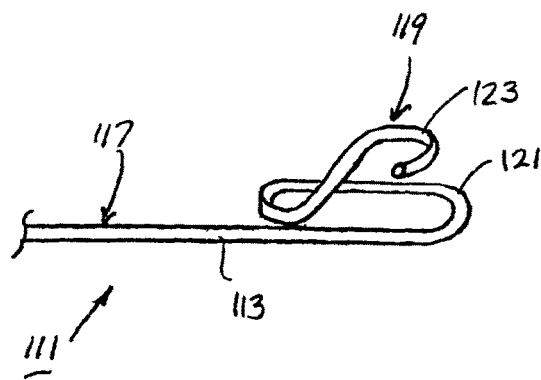
FIG. 4 is fragmentary, front perspective view of another embodiment of a preformed guidewire constructed according to the teachings of the present invention, details in the outer cover not being shown for ease of illustration.

For instance, referring now to FIG. 4, there is shown another embodiment of a preformed guidewire that is constructed according to the teachings of the present invention, the guidewire being identified generally by reference numeral 111. As can be seen, guidewire 111 is similar to guidewire 11 in that guidewire 111 includes an inner corewire 113 that is shaped to include a straightened proximal region 117 and a flexible distal region 119 that is formed into an encircled S-shaped configuration. Additionally, flexible distal region 119 similarly includes a proximal segment 121 that encircles a distal segment 123, with proximal segment 121 and distal segment 123 curving in opposite directions.

Inner corewire 113 differs from corewire 13 in that corewire 113 is shaped such that proximal segment 121 lies in a primary plane, whereas distal segment 123 deflects away from proximal segment 121 and enters into a secondary plane. As can be appreciated, the multi-planar construction of distal region 119 minimizes the likelihood of entanglement of distal region 119 with mitral valve substructures.

Distal region 19 of corewire 13 is preferably shaped, or otherwise formed, through a thermal shape setting process. As part of the process, distal region 19 is inserted into a sleeve that is shaped into the optimized configuration. Heat is then applied to distal region 19 of corewire 13 through the sleeve for a short period of time. Once cooled and removed from the sleeve, corewire 13 is permanently imparted with the optimized shape. Accordingly, although corewire 13 can be reconfigured upon applying a suitable force thereon (e.g., straightened from insertion through a guide catheter), the thermal treatment of the shape-memory material causes distal region 19 of corewire 13 to resiliently return to its preformed, optimized configuration.

It is to be understood that guidewire 11 could be readily constructed using a plurality of predefined manufacturing stages. For instance, in the first step, a length of corewire 13 is supplied and cut to a proper length (e.g., approximately 260 cm). Outer coating 25 is then applied to proximal region 17. Thereafter, distal region 19 and transition region 21 are formed into their designated cross-sectional profiles through a grinding process. Once completed, distal region 19 is shaped into its optimized, encircled S-shaped configuration through a thermal shape setting process. Outer casing 15 is then slid over distal region 19 of corewire 13 and secured at each end 33 using an appropriate bonding agent, thereby completing the manufacturing process.

Figure 5A:
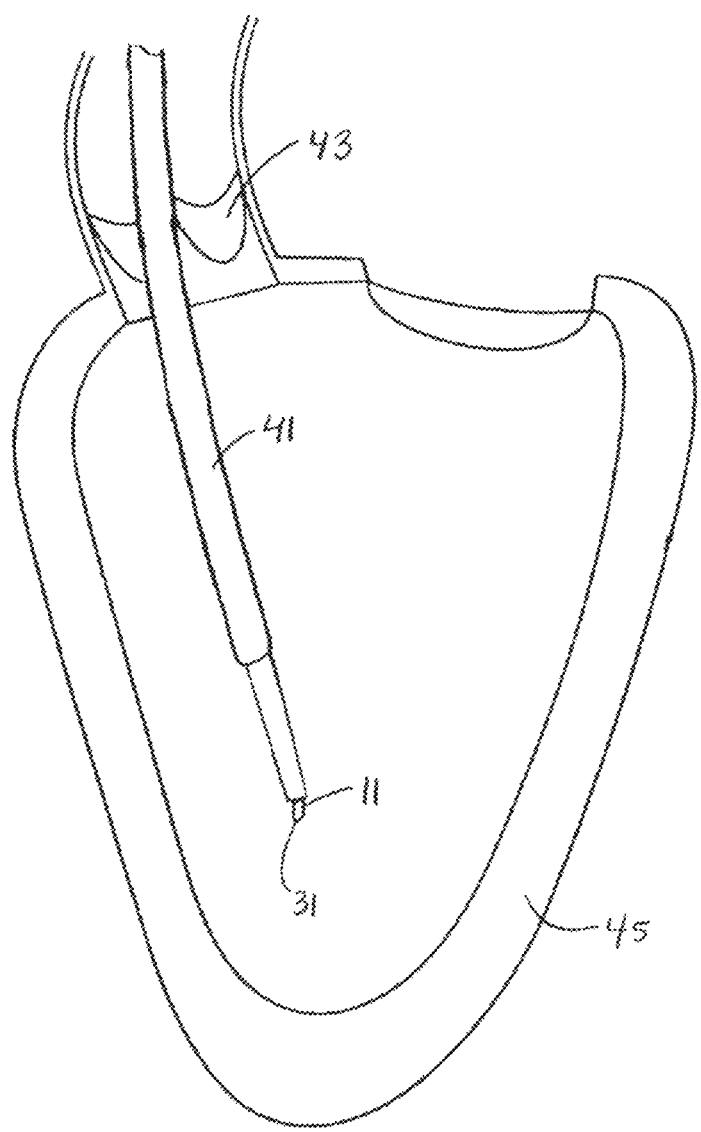
Figure 5B:
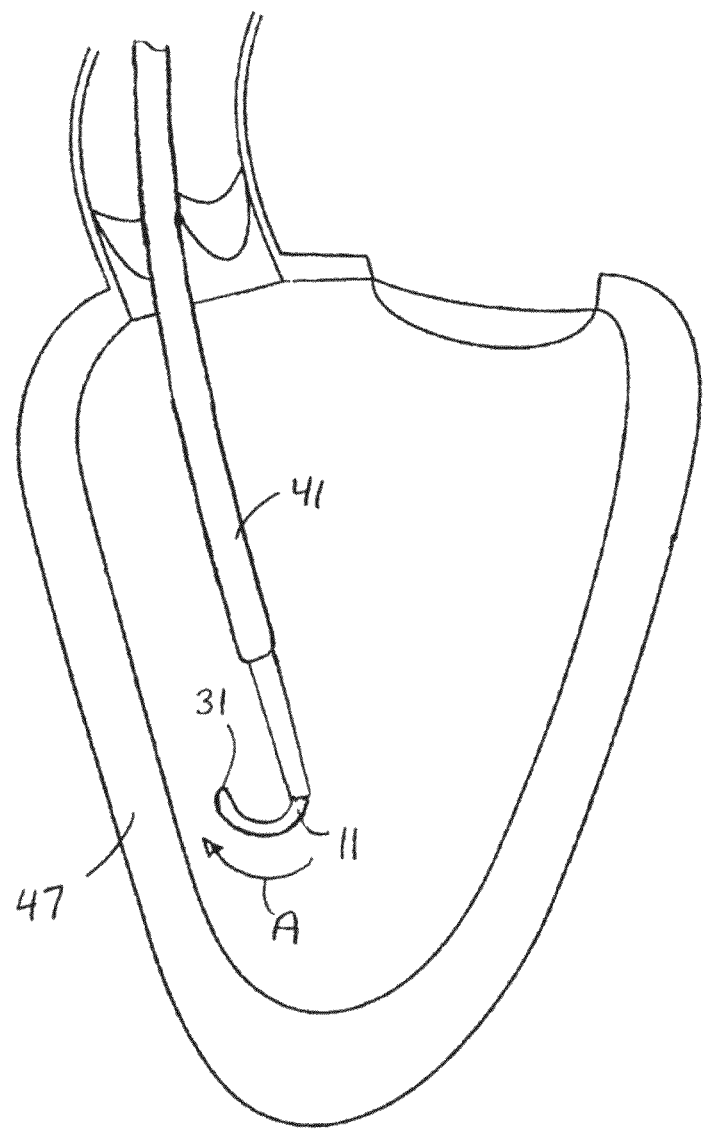

Referring now to FIGS. 5(a)-(d), guidewire 11 can be used in the following manner as a support structure for transcatheter aortic valve implantation. Specifically, as shown in FIG. 5(a), a guide catheter 41 is positioned within the aortic valve 43. Guidewire 11 is then inserted through guide catheter 41 until tip 31 projects into left ventricle 45.

Figure 5C:
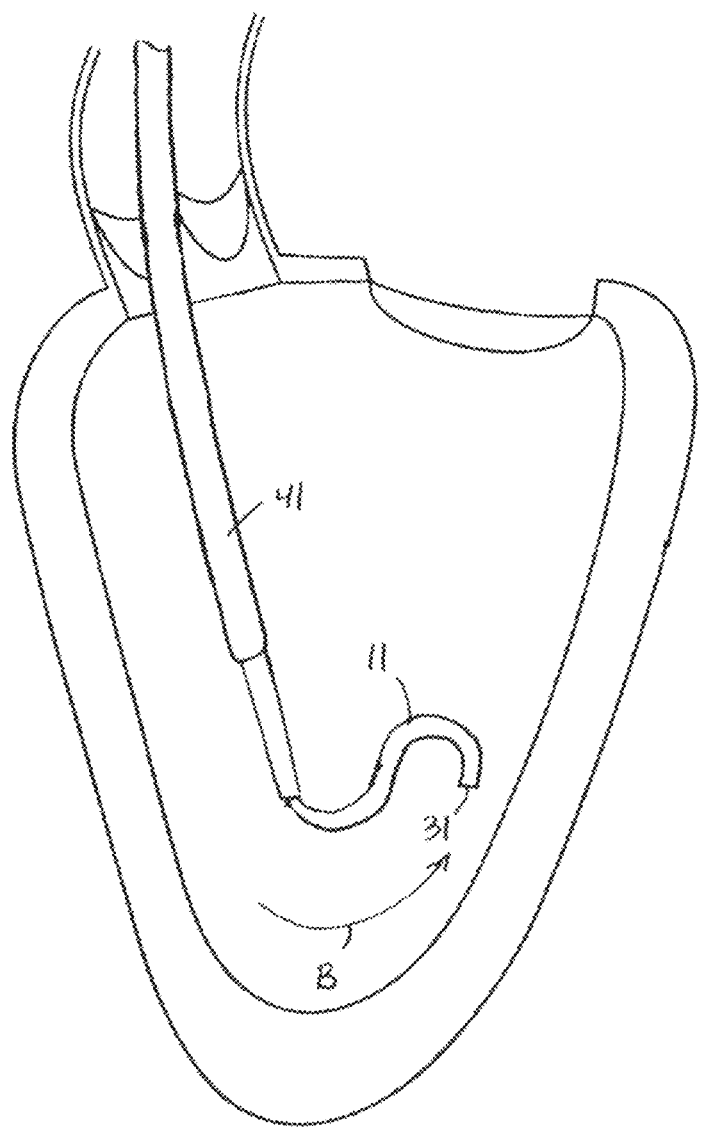
Figure 5A:
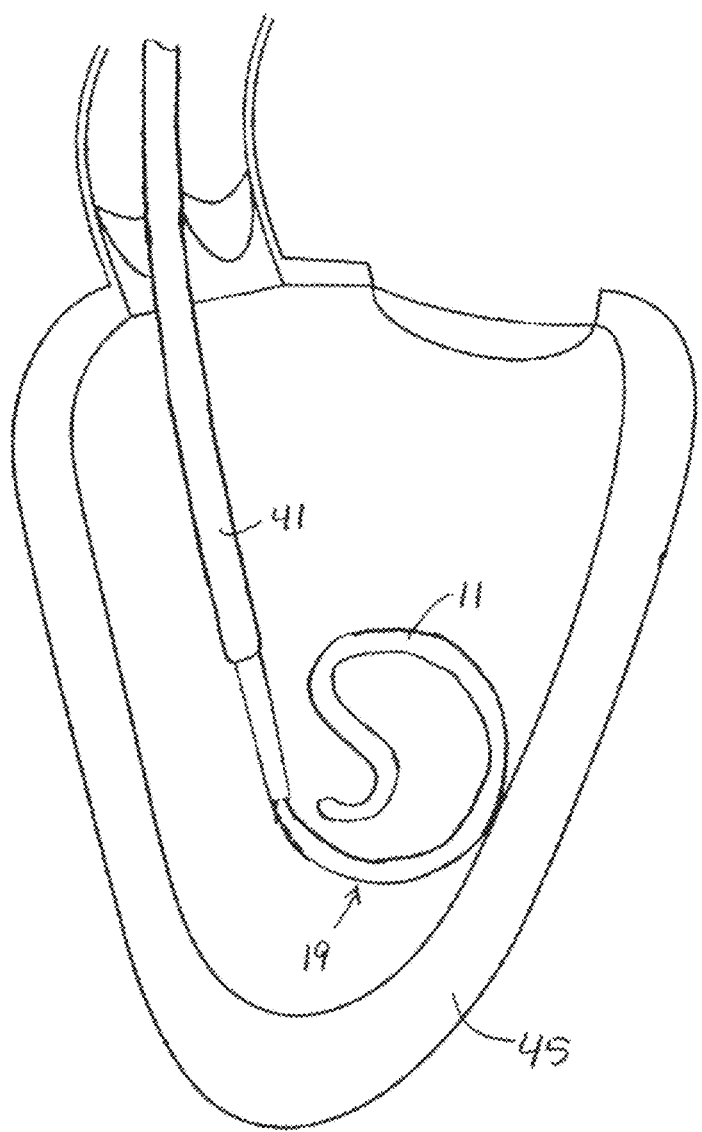

As shown in FIG. 5(h), further advancement of guidewire 11 through catheter 41 causes tip 32 (and its surrounding outer casing 15) to travel along a primary arcuate path, the direction of the primary path being represented by arrow A. Referring now to FIG. 5(c), the continued advancement of guidewire 11 through catheter 41 causes tip 32 to then reverse direction and travel along a secondary arcuate path that runs opposite to primary arcuate path, the direction of secondary path being represented by arrow B. In this capacity, if tip 32 initially catches on myocardium 47 as it travels along the primary arcuate path, the subsequent reversal in direction of tip 32 as it travels along the secondary path would cause tip 32 to withdraw from the myocardium 47, thereby limiting damage caused thereto.

With guidewire 11 fully advanced through guide catheter 41, distal region 19 resiliently returns to its preformed configuration, as shown in FIG. 5(d). Configured as such, atraumatic distal region 19 is appropriately designed to locate, or nest, against the base of left ventricle 45. Guide catheter 41 can then be removed from guidewire 11. Anchored as such within left ventricle 45, guidewire 11 can then be used to provide support for the aortic valve implantation procedure.

The embodiments shown above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A preformed guidewire comprising a continuous inner corewire, the inner corewire being solid and including a proximal region and a distal region, the distal region including and terminating into an atraumatic tip, > wherein the distal region includes a proximal segment and a distal segment,
>
> wherein the proximal segment of the distal region and the distal segment of the distal region are preformed to form adjoining curves of an S-shaped structure and wherein the proximal segment of the distal region is additionally preformed to encircle the distal segment of the distal region, whereby the distal region forms a preformed encircled S-shaped structure, wherein, as part of the preformed encircled S-shaped structure, the proximal segment of the distal region extends along a first generally circular path at least 270 degrees in a first direction, the distal segment of the distal region extends along a second generally circular path at least 180 degrees in a second direction, and the atraumatic tip is located within the curvature of the proximal segment, one of the first direction and the second direction being a clockwise direction as viewed from a proximal end of the distal segment to a distal end of the distal segment, the other of the first direction and the second direction being a counterclockwise direction as viewed from the proximal end of the distal segment to the distal end of the distal segment,
>
> wherein the atraumatic tip comprises a first tapered portion, a second tapered portion, and a first barrel portion, wherein the first barrel portion directly adjoins each of the first tapered portion and the second tapered portion, wherein the first tapered portion is disposed proximal to the first barrel portion and tapers in thickness distally to the first barrel portion, wherein the second tapered portion is disposed distal to the first barrel portion and tapers in thickness proximally to the first barrel portion, and wherein the atraumatic tip is formed solely from the inner corewire,
>
> wherein the distal region of the inner corewire is resilient and is constructed to straighten when subjected to a straightening force and to revert from straightened to the preformed encircled S-shaped structure, when no external force is applied thereto after being inserted distally through a guide catheter, first by having the atraumatic tip travel along a primary arcuate path and then by having the atraumatic tip travel along a second arcuate path, the secondary arcuate path being opposite in direction to the primary arcuate path,
>
> wherein, when the inner corewire is straightened, the atraumatic tip is capable of coming into direct contact with tissue,
>
> wherein the inner corewire has a reduction in cross-section along a length distal to the proximal region and proximal to the atraumatic tip, wherein the reduction in cross-section of said length of the inner corewire is gradual and discontinuous and comprises a first tapered section, a second tapered section, and a first barrel section, the first and second tapered sections being spaced apart by the first barrel section, each of the first and second tapered sections tapering distally, the reduction in cross-section rendering the distal region more flexible in construction than the proximal region, and
>
> wherein the distal region lies in a single plane.

2. The preformed guidewire as claimed in claim 1 wherein the first generally circular path is approximately 360 degrees in the first direction.

3. The preformed guidewire as claimed in claim 2 wherein the proximal segment has an overall diameter of approximately 1.2 inches.

4. The preformed guidewire as claimed in claim 1 wherein the inner corewire is constructed of a shape-memory material.

5. The preformed guidewire as claimed in claim 4 wherein the inner corewire is constructed of a nickel-titanium alloy.

6. The preformed guidewire as claimed in claim 1 wherein the first barrel portion enables the tip to buckle upon receiving a sufficient application of force.

7. The preformed guidewire as claimed in claim 1 further comprising an outer casing that surrounds at least a portion of the inner corewire.

8. The preformed guidewire as claimed in claim 7 wherein the outer casing surrounds the distal region of the corewire.

9. The preformed guidewire as claimed in claim 8 wherein the outer casing has a uniform, outer diameter along the entirety of its length.

10. The preformed guidewire as claimed in claim 9 wherein the outer casing is in the form of a spring coil wire with a first end and a second end, wherein each of the first and second ends is secured to the inner corewire by a bonding agent.

11. The preformed guidewire as claimed in claim 1 wherein the proximal region of the corewire is applied with an outer coating to increase lubricity.

12. The preformed guidewire as claimed in claim 1 wherein the atraumatic tip further comprises a second barrel portion and a third barrel portion, wherein the second barrel portion directly adjoins and is disposed proximal to the first tapered portion, and wherein the third barrel portion directly adjoins and is disposed distal to the second tapered portion.

13. The preformed guidewire as claimed in claim 1 wherein each of the first tapered portion and the second tapered portion has a maximum diameter and wherein the maximum diameter of the second tapered portion is greater than the maximum diameter of the first tapered portion.

14. The preformed guidewire as claimed in claim 1 wherein said length of the inner corewire distal to the proximal region and proximal to the atraumatic tip further comprises a third tapered section and a second barrel section, the third tapered section tapering distally and being spaced apart from the first tapered section by the second barrel section, the tapered sections and the barrel sections arranged in an alternating, end-to-end fashion.

* * * * *